US007147170B2

(12) United States Patent
Nguyen et al.

(10) Patent No.: US 7,147,170 B2
(45) Date of Patent: Dec. 12, 2006

(54) AEROSOL GENERATING DEVICE AND METHOD OF USE THEREOF

(75) Inventors: Tung T. Nguyen, Midlothian, VA (US); Douglas D. McRae, Chesterfield, VA (US); Kenneth A. Cox, Midlothian, VA (US); Walter A. Nichols, Chesterfield, VA (US); Ulysses Smith, Midlothian, VA (US); Gary E. Grollimund, Chesterfield, VA (US); Donald L. Brookman, Richmond, VA (US)

(73) Assignee: Philip Morris USA Inc., Richmond, VA (US)

( * ) Notice: Subject to any disclaimer, the term of this patent is extended or adjusted under 35 U.S.C. 154(b) by 329 days.

(21) Appl. No.: 10/655,017

(22) Filed: Sep. 5, 2003

(65) Prior Publication Data

US 2004/0129793 A1    Jul. 8, 2004

Related U.S. Application Data

(60) Provisional application No. 60/408,295, filed on Sep. 6, 2002.

(51) Int. Cl.
*B05B 1/24* (2006.01)
*A61M 11/00* (2006.01)

(52) U.S. Cl. .................. 239/13; 239/136; 239/135; 239/338; 239/68; 239/69; 128/200.14

(58) Field of Classification Search ............... 239/13, 239/136, 135, 338, 68, 69, 67, 70, 71, 74, 239/128, 337; 128/200.14, 203.17, 203.25, 128/203.26, 203.27
See application file for complete search history.

(56) References Cited

U.S. PATENT DOCUMENTS

| 4,383,171 | A |   | 5/1983  | Sinha et al.           |
|-----------|---|---|---------|------------------------|
| 4,472,133 | A | * | 9/1984  | Petersen et al. .......... 431/3 |
| 4,512,341 | A |   | 4/1985  | Lester                 |
| 5,743,251 | A |   | 4/1998  | Howell et al.          |
| 6,155,268 | A | * | 12/2000 | Takeuchi ............ 131/273 |
| 6,159,188 | A |   | 12/2000 | Laibovitz et al.       |
| 6,197,835 | B1 |  | 3/2001  | Gañan-Cálvo           |
| 6,234,167 | B1 |  | 5/2001  | Cox et al.             |
| 6,295,986 | B1 |  | 10/2001 | Patel et al.           |

(Continued)

FOREIGN PATENT DOCUMENTS

WO    WO01/21319 A1    3/2001

OTHER PUBLICATIONS

"Proceedings of the Royal Society of London, Series A, Mathematical, Physical and Engineering Sciences/the Royal Society," Proceedings of the Royal Society of London SERIES A, vol. 454 No. 1977, Sep. 8, 1996, pp. 2279-2533.

(Continued)

*Primary Examiner*—Davis Hwu
*Assistant Examiner*—Darren Gorman
(74) *Attorney, Agent, or Firm*—Buchanan Ingersoll & Rooney PC

(57) ABSTRACT

An aerosol generating device generates an aerosol having a desired particle size by passing a liquid through a flow passage heated to convert the liquid into a vapor. The flow passage includes an outlet section that controls the exit velocity of the vapor and produces an aerosol with a desired particle size. The aerosol generator can be incorporated in a hand held inhaler, and the liquid can include a medicament, which is delivered to a targeted portion of the lung using the inhaler.

43 Claims, 8 Drawing Sheets

U.S. PATENT DOCUMENTS

| | | | |
|---|---|---|---|
| 6,318,361 B1 | 11/2001 | Sosiak | |
| 6,528,018 B1 | 3/2003 | Berndt | |
| 6,568,390 B1 * | 5/2003 | Nichols et al. | 128/203.16 |
| 6,598,602 B1 * | 7/2003 | Sjöholm | 128/200.16 |
| 6,681,769 B1 * | 1/2004 | Sprinkel et al. | 128/203.26 |
| 6,681,998 B1 * | 1/2004 | Sharpe et al. | 239/13 |
| 6,701,921 B1 * | 3/2004 | Sprinkel et al. | 128/203.26 |
| 6,701,922 B1 * | 3/2004 | Hindle et al. | 128/203.27 |
| 6,883,516 B1 * | 4/2005 | Hindle et al. | 128/200.14 |
| 2002/0079309 A1 | 6/2002 | Cox et al. | |
| 2002/0079377 A1 | 6/2002 | Nichols | |

OTHER PUBLICATIONS

J. R. Brock et al., "Condensation Aerosol Formation and Growth in a Laminar Coaxial Jet: Experimental", J. Aerosol Science, vol. 17 No. 1, pp. 11-22, 1986.

W. Koch et al., "Modeling and Experimental Evaluation of an Aerosol Generator for Very High Number Currents Based on a Free Turbulent Jet", J. Aerosol Sci., vol. 24, No. 7 pp. 909-918, 1993.

Notification of Transmittal of the International Search Report or the Declaration dated Dec. 24, 2003 for PCT/US03/27729.

Notification of Transmittal of International Preliminary Examination Report dated Jun. 18, 2004 for PCT/US03/27729.

\* cited by examiner

AEROSOL GENERATING DEVICE AND METHOD OF USE THEREOF

RELATED APPLICATIONS

This application claims priority under 35 U.S.C. § 119 to U.S. Provisional Application No. 60/408,295, entitled AEROSOL GENERATING DEVICE AND METHOD OF USE THEREOF and filed on Sep. 6, 2002, the entire content of which is hereby incorporated by reference.

BACKGROUND

Aerosols are gaseous suspensions of fine solid or liquid particles. Aerosols are useful in a wide variety of applications. For example, medicated liquids may be administered in aerosol form. Medicated aerosols include materials that are useful in the treatment of respiratory ailments. In such applications, the aerosols may be produced by an aerosol generator and inhaled into a patient's lungs. Aerosols are also used in non-medicinal applications including, for example, dispensing air fresheners and insecticides and delivering paints and lubricants.

Aerosol generators are known that include a heated tube for vaporizing liquid. For example, commonly assigned U.S. Pat. No. 5,743,251, which is incorporated herein by reference in its entirety, discloses an aerosol generator including a tube and a heater operable to heat the tube to a sufficient temperature to volatilize liquid in the tube. The volatilized material expands out of an end of the tube and admixes with ambient air, thereby forming an aerosol.

As shown in FIG. 1, an aerosol generator 21 disclosed in U.S. Pat. No. 5,743,251 includes a tube 23 defining a capillary sized fluid passage and having an open end 25. A heater 27 is positioned adjacent to the tube 23. The heater 27 is connected to a power supply 29. The tube 23 also includes an inlet end 31 in fluid communication with a source 33 of liquid material. In operation, liquid is introduced into the tube 23. The heater 27 heats a portion of the tube 23 to a sufficiently high temperature to volatilize the liquid. The volatilized material expands out of the open end 25 of the tube. The volatilized material admixes with ambient air and condenses to form a condensation aerosol.

Other exemplary aerosol generators including a heated tube for vaporizing liquids to produce a condensation aerosol are disclosed in commonly assigned U.S. patent application Ser. No. 09/956,966 filed Sep. 21, 2001 and Ser. No. 10/003,437 filed Dec. 6, 2001, and in commonly assigned U.S. Pat. No. 6,234,167, the disclosure of each being incorporated herein by reference in its entirety.

SUMMARY

An aerosol generating device that can produce aerosols having a desired particle size from liquids is provided.

An embodiment of an aerosol generating device comprises a liquid source and a flow passage including an outlet section in fluid communication with the liquid source. A heater is disposed to heat liquid in the flow passage to produce vapor. The outlet section is configured to change the velocity of vapor in the flow passage such that the vapor exits the outlet section at a controlled exit velocity. The vapor is admixed with air to produce an aerosol after exiting the outlet section.

The outlet section of the flow passage can be configured either to increase, or to decrease, the exit velocity of the vapor. By controlling the exit velocity of the vapor, the aerosol generating device can produce aerosols having a controlled particle size from various liquids. The portion of the flow passage heated by the heater is preferably capillary sized.

An exemplary embodiment of a method of generating an aerosol comprises supplying a liquid to a flow passage including an outlet section; heating liquid in the flow passage to produce a vapor; and changing the velocity of the vapor in the flow passage in the outlet section such that the vapor exits the outlet section at a controlled exit velocity. The vapor exiting the outlet section is admixed with air to produce an aerosol with a desired particle size.

DRAWINGS

DETAILED DESCRIPTION

An aerosol generating device is provided. The aerosol generating device can have different constructions and sizes and can be used to produce aerosols having different particle sizes.

The aerosol generating device can produce aerosols having controlled particle sizes, making it suitable for different applications. For example, for drug delivery to the human lung, the desired mass mean aerodynamic diameter (MMAD) of an aerosol depends on the portion of the lung to which the aerosol is desired to be delivered. Generally, aerosols having a smaller MMAD are capable of deeper lung penetration than aerosols having a larger MMAD. The aerosol generating device can produce aerosols having a controlled particle size that is effective to efficiently deliver drug formulations to selected regions of the lung.

In a preferred embodiment of the aerosol generating device, a medicated liquid is flowed through a capillary sized flow passage in which the liquid is heated to a sufficiently high temperature to vaporize the liquid. The vapor exits the flow passage and admixes with gas, typically ambient air, to produce an aerosol, which is inhaled by a user. The size of the aerosol particles thus produced can be controlled for delivery to a targeted region of the lung.

Figure 1:
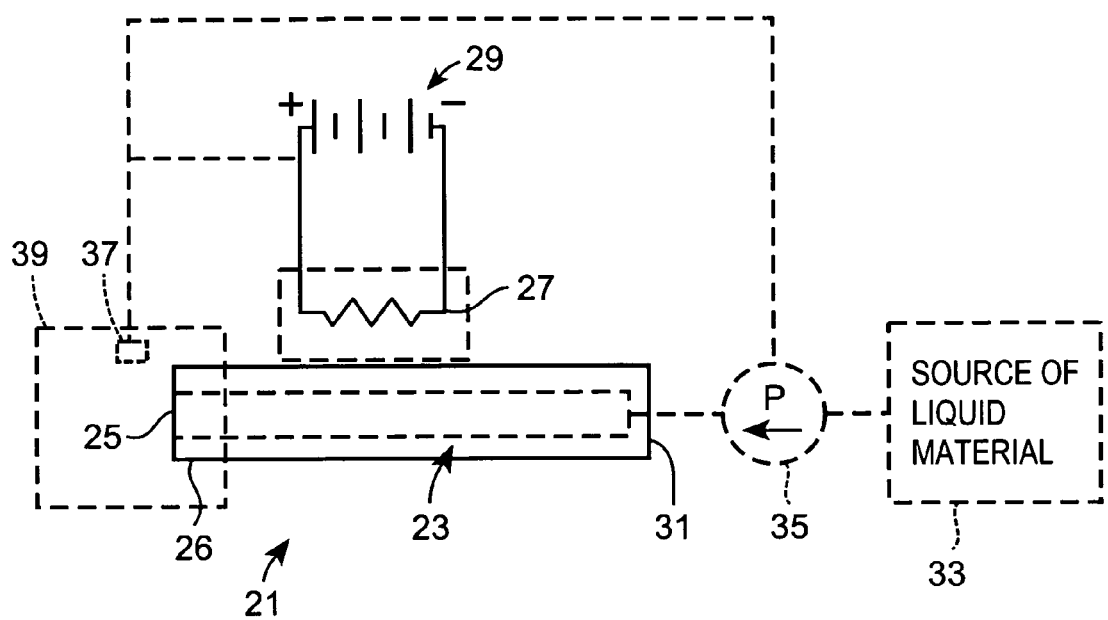
FIG. 1 illustrates an aerosol generator having a heated capillary passage according to the prior art.
Figure 2:
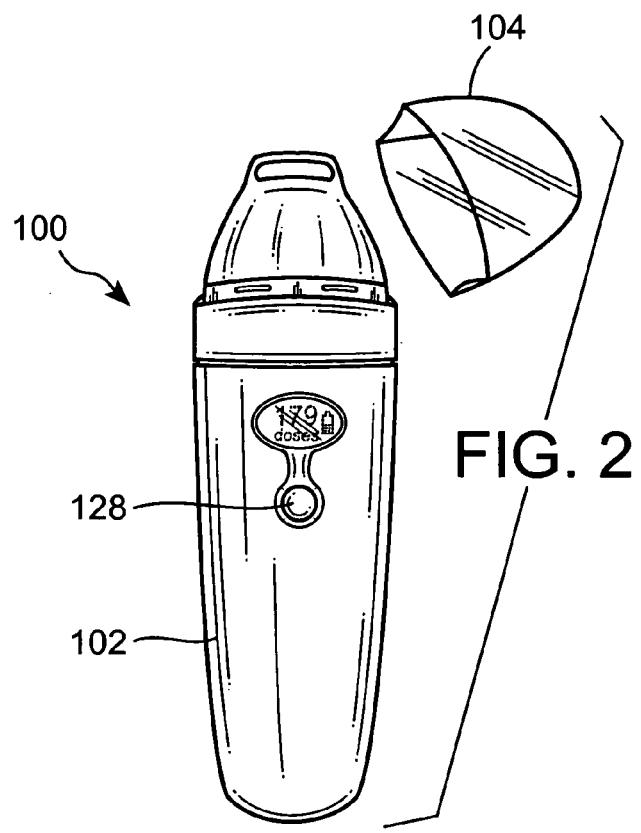
FIG. 2 is a perspective view of an embodiment of handheld aerosol generating device (inhaler) with the cap removed.
Figure 3:
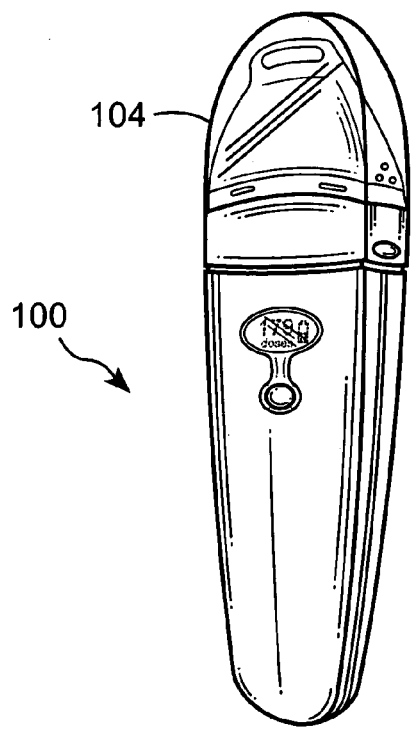
FIG. 3 shows the aerosol generating device of FIG. 2 with the cap installed.
Figure 4:
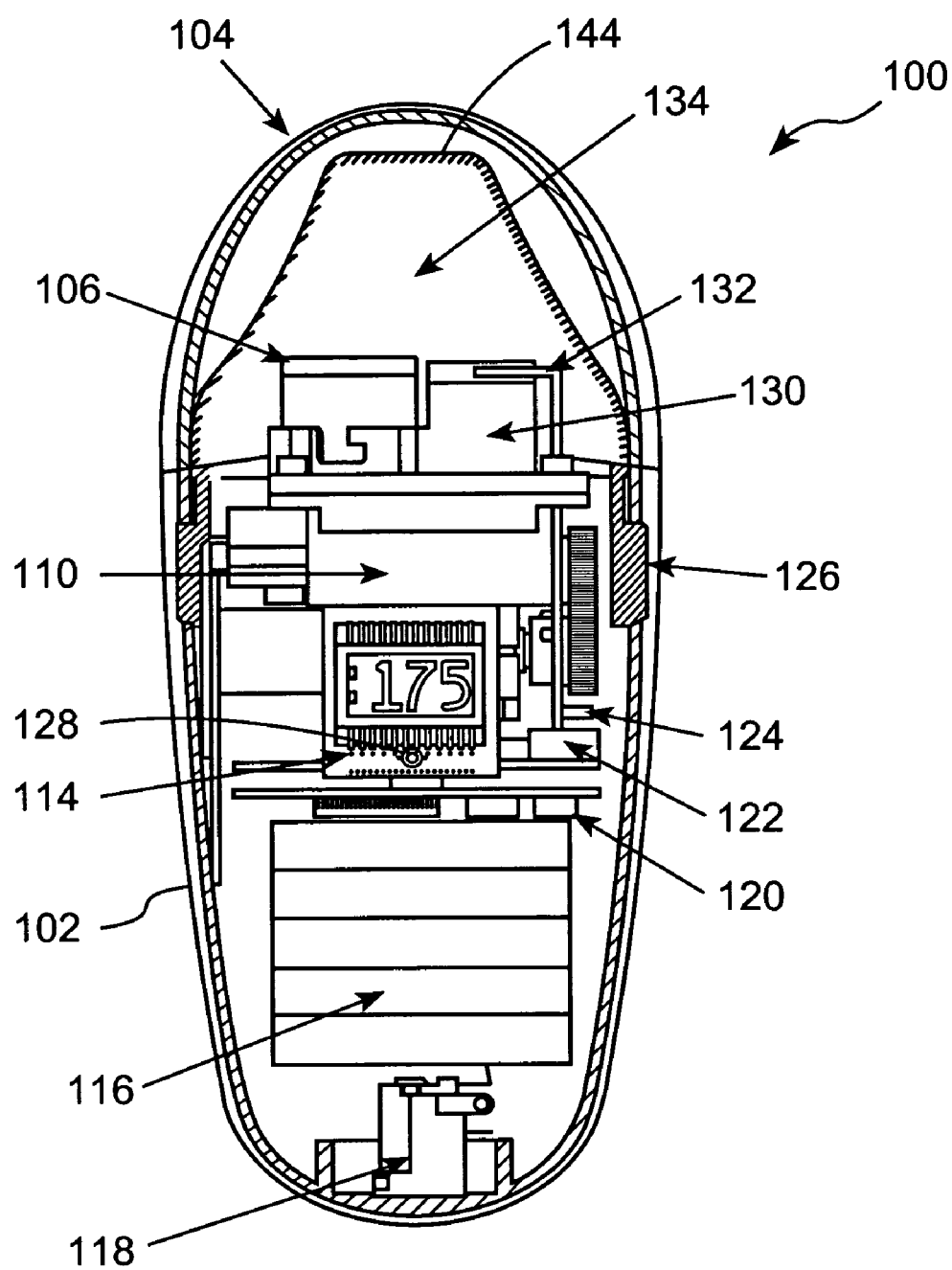
FIG. 4 illustrates an embodiment of an aerosol generating device.

FIGS. 2–4 illustrate an exemplary embodiment of an aerosol generating device 100. The aerosol generating device 100 includes a housing 102; a removable protective cap 104, which activates a master on/off switch, (not shown); a fluid delivery assembly 110 including a liquid source 106 and a heater unit 130; a display 114; a battery unit 116; a charging jack 118; control electronics 120; a pressure sensor 122; an air inlet 124; a release 126 for detaching the fluid delivery assembly 110 from the aerosol generating device 100; a manually actuated master activation switch 128; an air passage 132 and a removable mouthpiece 134. FIG. 2 shows the cap 104 removed from the aerosol generating device 100, while FIG. 3 shows the cap installed.

The housing 102, cap 104, and mouthpiece 134 are preferably made of a polymeric material. These parts may be fabricated by plastic injection molding, or by any other suitable technique. The housing 102 can be fabricated in an ergonmetric configuration that is comfortable to hold by a user.

In a preferred embodiment, the fluid delivery assembly 110 is removably attachable to a portion of the aerosol generating device 100 by any suitable attachment construction. For example, the fluid delivery assembly 110 can be attached by a mechanical connection, such as a snap-fit engagement, or by a twist-on engagement. For example, conductive contacts (not shown) can be provided in the aerosol generating device to make electrical contact with the heater unit 130, when the fluid delivery assembly 110 is attached to the aerosol generating device. In such embodiments, the fluid delivery assembly 110, which includes the wetted components of the aerosol generating device, can be replaced in the vapor generating device as a complete unit. As described below, the fluid delivery assembly 110 can provide aerosols having a controlled particle size. Different fluid delivery assemblies 110 that can provide aerosols having different compositions and/or particle sizes can be interchanged in the aerosol generating device.

The fluid delivery assembly 110 can be replaced after liquid contained in the liquid source 106 has been consumed. A fluid delivery assembly 110 including a liquid source containing the same or a different medicament, and that produces the same or a different aerosol particle size, can then be installed in the aerosol generating device.

Figure 5:
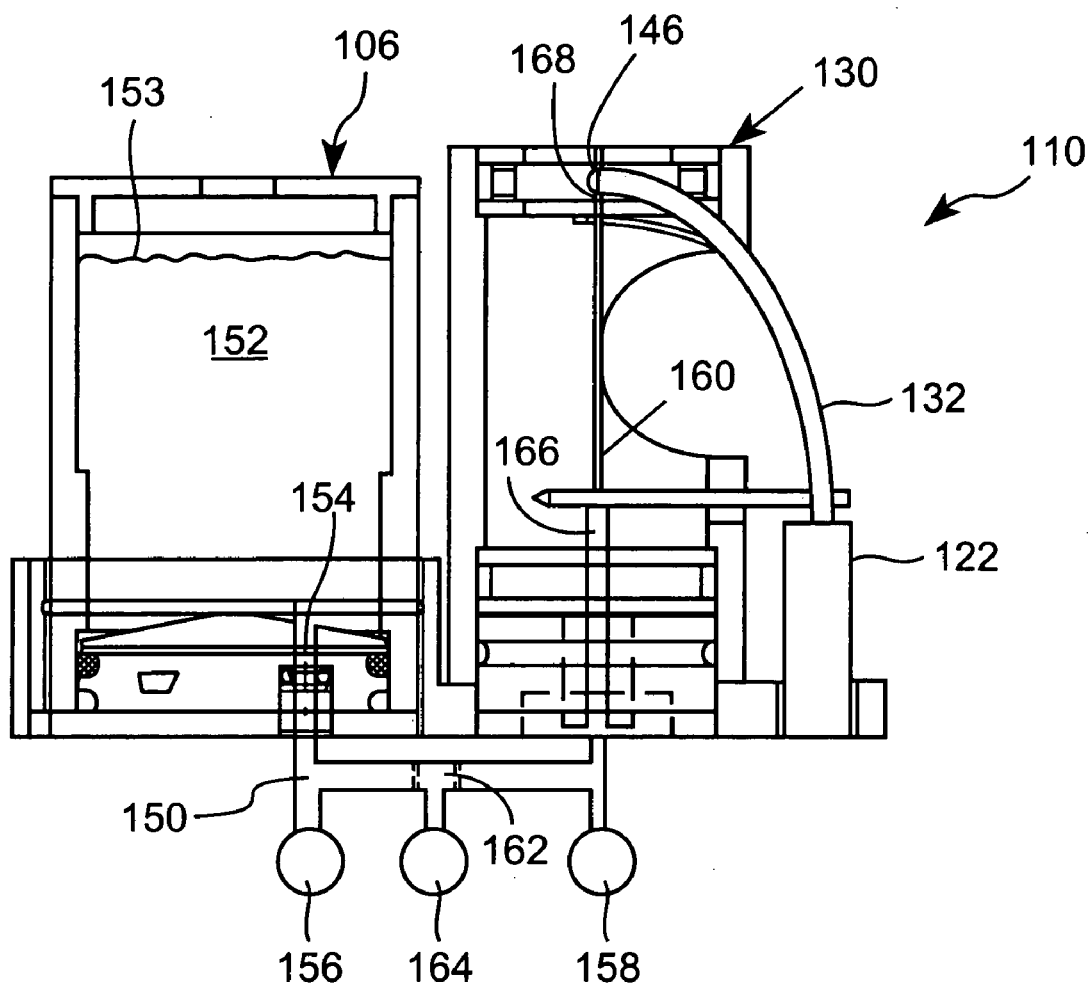
FIG. 5 illustrates an embodiment of the fluid delivery assembly of the aerosol generating device.

FIG. 5 illustrates a portion of the fluid delivery assembly 110, including a liquid source 106 and heater unit 130. Liquid is supplied from the liquid source 106 to the heater unit 130 through a flow passage 150.

The liquid source 106 comprises a reservoir 152 for containing a volume of liquid 153. In an embodiment, the liquid source 106 has a liquid capacity for delivering a selected number of doses of a selected volume. For example, the doses can be 5 μl doses and the reservoir 152 can be sized to contain multiple doses. Preferably, the liquid source can contain from about 10 doses to about 500 doses, e.g., 50 to 250 doses. However, the dose capacity of the liquid source is not limited and depends on the desired dose volume, which can be determined by the desired application of the aerosol generating device. The liquid contained in the liquid source can be any liquid that can be vaporized and aerosolized in the aerosol generating device to produce a desired aerosol. In a preferred embodiment, the liquid contains a medicament formulated to be inhaled into the user's lungs in aerosol form.

The liquid source 106 includes a flow passage 154, which provides fluid communication from the reservoir 152 to the flow passage 150. The aerosol generating device 100 includes at least one valve disposed to control flow of the liquid from the liquid source 106 into the heater unit 130. For instance, the aerosol generating device may include a single valve (not shown) to control flow of the liquid in the flow passage, or a plurality of valves. In a preferred embodiment, the aerosol generating device includes an inlet valve 156 and an outlet valve 158. The inlet valve 156 is operable to open and close an inlet of the flow passage 150, which controls the supply of liquid from the liquid source 106 into the flow passage 150. The outlet valve 158 is operable to open and close an outlet end of the flow passage 150, which controls the supply of liquid from the flow passage 150 into a heated flow passage.

The aerosol generating device 100 preferably includes a metering chamber 162 located in the flow passage 150 between the inlet valve 156 and the outlet valve 158. The metering chamber 162 is preferably sized to contain a predetermined volume of the liquid. For example, the metering chamber can be sized to contain a volume of the liquid that corresponds to one dose of the aerosolized medicament. A discharge member 164 can be used to open the metering chamber 162 during a liquid filling cycle, and to empty the metering chamber during a liquid delivery cycle, as described in greater detail below.

The heater unit 130 of the fluid delivery assembly 110 comprises a heated flow passage 160. The flow passage 160 is preferably a capillary sized flow passage, referred to hereinafter as a "capillary passage." The capillary passage 160 forms a portion of the entire flow passage in the aerosol generating device 100. The capillary passage 160 includes an open inlet end 166, and an opposite open outlet end 168. During operation of the aerosol generating device 100, liquid is supplied into the capillary passage 160 at the inlet end 166 from the flow passage 150.

The capillary passage 160 can have different transverse cross-sectional shapes, such as round, oval, triangular, square, rectangular, other polygonal shapes, or the like, as well as other non-geometric shapes. Different portions of the capillary passage can have different cross-sectional shapes. As described below, the size of the capillary passage 160 can be defined by its transverse cross-sectional area. For a capillary passage 160 having a round cross-section, the size of the flow passage may be defined by its diameter. Alternatively, the capillary passage may be non-circular in cross section and the size of the capillary passage 160 may be defined by its width. For example, the capillary passage can have a maximum width of 0.01 to 10 mm, preferably 0.05 to 1 mm, and more preferably 0.1 to 0.5 mm. Alternatively, the capillary passage can be defined by its transverse cross sectional area, which can be $8 \times 10^{-5}$ to 80 mm$^2$, preferably $2 \times 10^{-3}$ to $8 \times 10^{-1}$ mm$^2$, and more preferably $8 \times 10^{-3}$ to $2 \times 10^{-1}$ mm$^2$.

The capillary passage 160 comprises an outlet section, which controls the velocity of vapor exiting the outlet end 168 of the capillary passage, i.e, the exit velocity of the vapor. As described below, the particle size of aerosol generated by the aerosol generating device 100 can be controlled by varying the exit velocity of the vapor.

FIGS. 6–9 illustrate several embodiments of the capillary passage 260, 360, 460, 560, respectively. Capillary passage 260 includes an inlet end 266, an outlet end 268, a first section 270, and an outlet section 272. In this embodiment, the outlet section 272 has a larger cross-sectional area than the first section 270 of the capillary passage 260. In embodiments, the outlet section can have the same or a different cross-sectional shape than other portions of the capillary passage. For example, capillary passage 260 has a round cross-section, and the outlet section 272 has a larger diameter than the first section 270. Accordingly, as liquid travels downstream and is vaporized in the capillary passage 260 in the direction from the inlet end 266 to the outlet end 268 as indicated by arrow A, the vapor moves through the first section 270 at a first velocity and then into the outlet section 272. In the outlet section 272, the velocity of the vapor is reduced to a lower velocity than in the first section 270 by the outlet section 272 having a larger cross-sectional area than the first section 270.

In other embodiments, the outlet section can have a smaller cross-sectional area than the first section of the capillary passage. For example, the capillary passage 360 shown in FIG. 7 includes an inlet end 366, an outlet end 368, a first section 370, and an outlet section 372. The outlet section 372 has a smaller cross-sectional area than the first section 370. Accordingly, the outlet section 372 increases the velocity of the vapor to a higher velocity than it has in the first section 370 as the vapor moves in the direction indicated by arrow A.

Accordingly, by selecting the cross-sectional area of the outlet section, the exit velocity of the vapor from the capillary passage is controlled by either increasing or decreasing the vapor velocity to a desired velocity. Consequently, the particle size of aerosol produced from vapor by the aerosol generating device can also be controlled, as described in greater detail below.

The capillary passage can have more than two sections having different cross-sectional areas from each other (not shown), i.e, more than one section that acts as an outlet section relative to the adjacent upstream section as the fluid moves through the capillary passage. For example, the capillary passage can include three sections having different cross-sectional areas from each other. In such embodiments, the cross-sectional area of the capillary passage can decrease or increase in size from the first section to the second section, and decrease or increase in size from the second section to the third section, i.e., the exit outlet section. Accordingly, the velocity of the fluid is changed (increased or decreased) as the fluid moves from the first section into the second section, and then changed again (increased or decreased) as it moves from the second section into the third section. The exit velocity of the vapor is controlled by the cross-sectional area of the third section.

Figure 6:
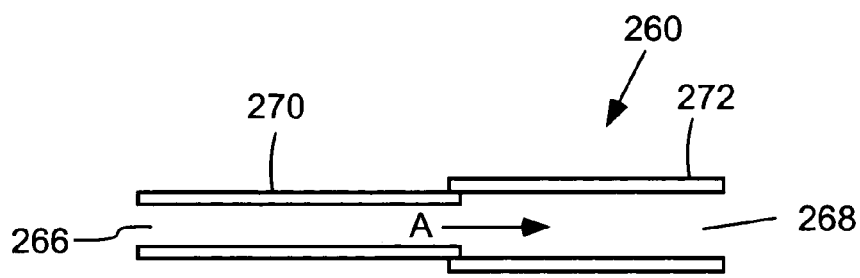
FIG. 6 illustrates a capillary passage including an outlet section having an enlarged cross-sectional area according to a first embodiment.
Figure 7:
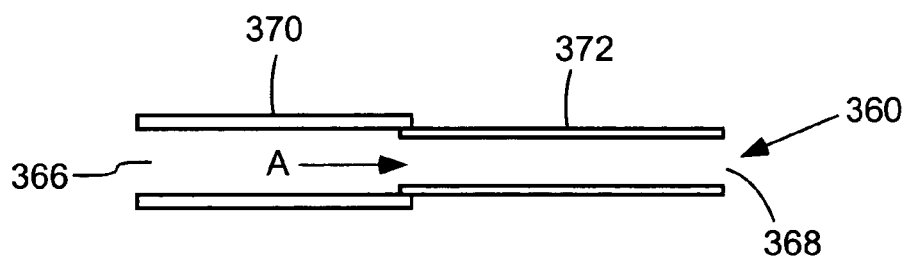
FIG. 7 illustrates a capillary passage including an outlet section having a reduced cross-sectional area according to a second embodiment.
Figure 8:
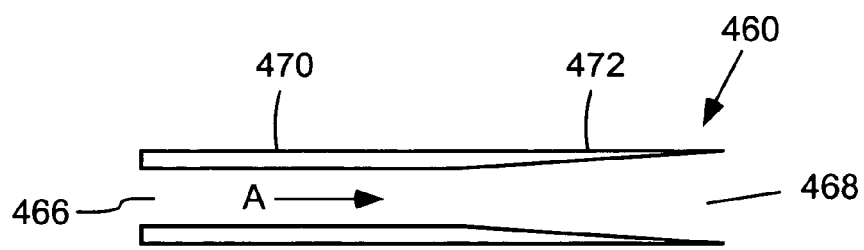
FIG. 8 illustrates a one-piece capillary passage including an outlet section according to a third embodiment.

In capillary passages 260, 360 shown in FIGS. 6 and 7, the cross-sectional area of the first section 270, 370, respectively, is constant along its length, and the cross-sectional area of the outlet section 272, 372, respectively, is also constant along its length. However, in other embodiments, the capillary passage can include one or more section(s) in which the cross-sectional area is not constant along the length of the section(s). For example, FIG. 8 shows an exemplary embodiment of the capillary passage 460 including an outlet section 472 in which the cross-sectional area of the capillary passage 461 changes (increases) along its length in a direction toward the outlet end 468. When the outlet section 472 is used, the vapor velocity through the outlet section 472 decreases in the flow direction indicated by the arrow A. In other embodiments of the capillary passage, the cross-sectional area of the outlet section can decrease along its length (not shown) to increase the exit velocity of the vapor.

Figure 9:
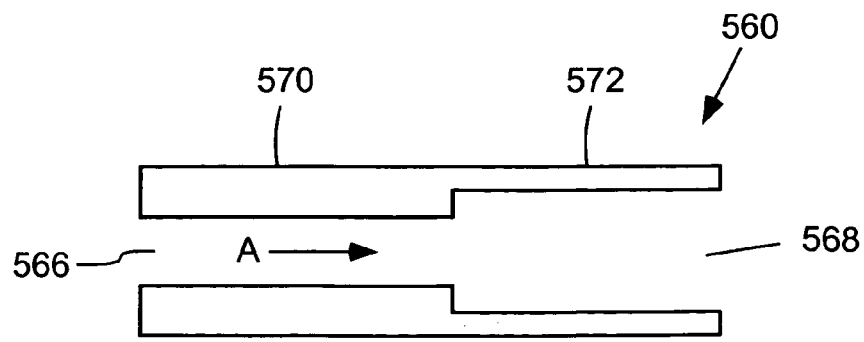
FIG. 9 illustrates a one-piece capillary passage including an outlet section according to a fourth embodiment.

In the capillary passage 460 shown in FIG. 8, the cross-sectional flow area of the outlet section 472 increases continuously along its length. However, the outlet sections of capillary passages can have shapes that provide an increasing or decreasing cross-sectional area of the capillary passage along the length of the outlet section. For example, as depicted in FIG. 9, the capillary passage 560 can alternatively have a stepped profile, including a portion in the first section 570 having a smaller cross-sectional area than a portion in the outlet section 572. In this embodiment, the velocity of the vapor decreases in the direction indicated by arrow A due to the increasing cross-sectional area of the capillary passage.

The material forming the capillary passage can be any suitable material, including metals, plastics, polymers, ceramics, glasses, or combinations of these materials. Preferably, the material is a heat-resistant material capable of withstanding the temperatures and pressures generated in the capillary passage, and also resisting the repeated heating cycles utilized to generate multiple doses of aerosols. In addition, the material forming the capillary passage preferably is non-reactive with the liquid that is aerosolized.

The capillary passages 460 and 560 shown in FIGS. 8 and 9 have a one-piece construction. The capillary passages 260 and 360 shown in FIGS. 6 and 7 have a two-piece construction. In embodiments that include two or more pieces, the pieces can be joined together in any suitable manner. The two or more pieces can be removably or fixedly attached to each other. For example, the capillary passage can comprise two or more pieces of tubing. In such embodiments, the size of the capillary passage defined in the outlet section can be either sufficiently large to receive another tube, or the outer diameter of the outlet section can be sufficiently small to fit within the bore of the other tube. Any suitable fastening material can be used to secure the pieces together and preferably provide a fluid seal. For example, any suitable adhesive can be used for this purpose. For joining sections made of metal, joining techniques, such as welding, soldering or brazing can be used. For other tube materials, any suitable joining material or technique that is compatible with the tube material can be used.

In another alternative embodiment, the capillary passage can be formed in a polymer, glass, metal and/or ceramic monolithic or multilayer (laminated) structure (not shown). Suitable ceramic materials for forming the capillary passage include, but are not limited to, alumina, zirconia, silica, aluminum silicate, titania, yttria-stabilized zirconia, or mixtures thereof. A capillary passage can be formed in the monolithic or multilayer body by any suitable technique, including, for example, machining, molding, extrusion, or the like.

In embodiments having a monolithic or multilayer structure, the capillary passage includes an outlet section having a cross-sectional flow area effective to achieve a desired exit velocity of the vapor. For example, the structure can include two separate monolithic bodies, including a first monolithic body defining a first capillary passage, and a second monolithic body defining a second capillary passage in flow communication with the first capillary passage, and sized to control the exit velocity of the vapor from the second capillary passage. The capillary passages in the different sections can have any suitable cross-sectional shape.

The length of the capillary passage is equal to the total length of the one or more sections that form it. In embodiments, the capillary passage can have a length from 0.5 to 10 cm, and preferably from 1 to 4 cm. In the capillary passages 460, 560 shown in FIGS. 8 and 9, respectively, the respective outlet sections 472, 572 are sufficiently long to decrease the velocity of the vapor moving in the capillary passage from a velocity, at which the vapor moves in the first section 470, 570, respectively, to the desired exit velocity at which the vapor exits the outlet end of the capillary passage.

Figure 10:
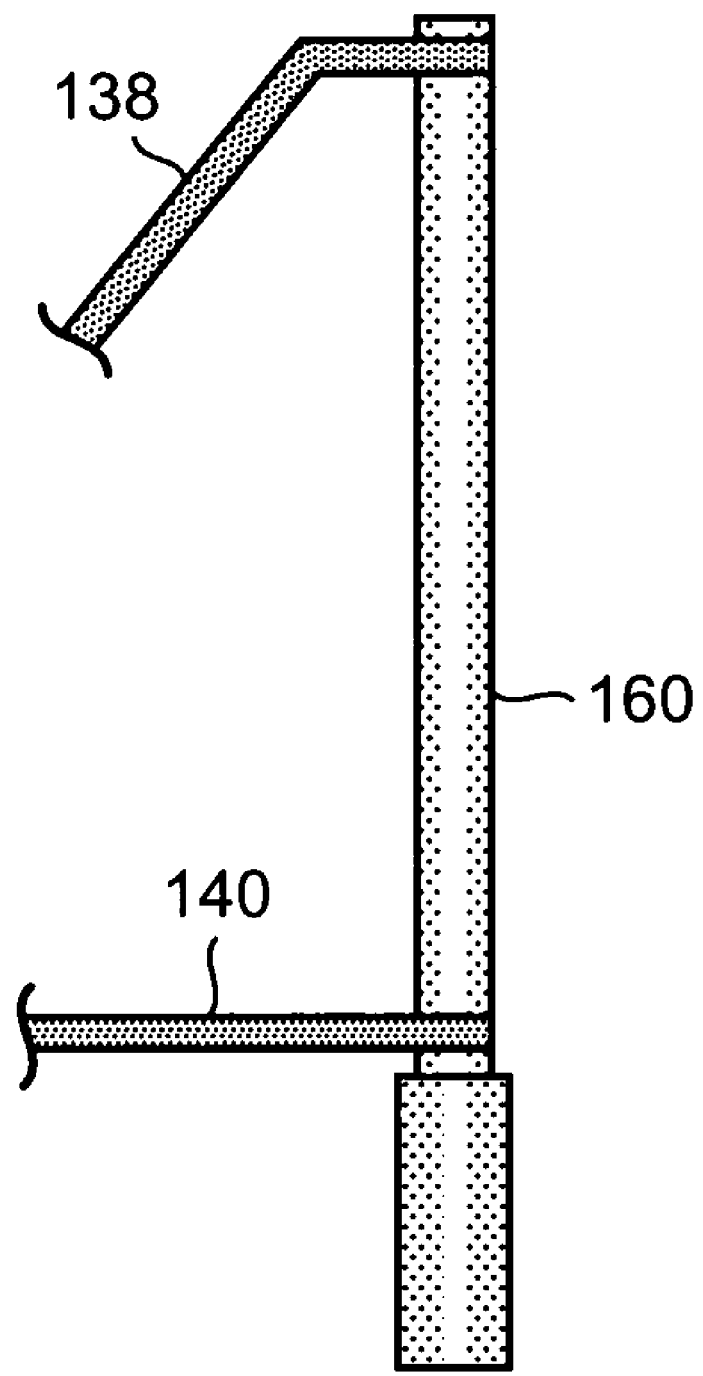
FIG. 10 illustrates an embodiment of the capillary passage including two electrodes.

The fluid supplied from the liquid source 106 is heated in the capillary passage to form a vapor during operation of the aerosol generating device 100. In a preferred embodiment shown in FIG. 10, the capillary 160 comprises metal tubing heated by passing an electrical current along a length of the capillary via a first electrode 138 and a second electrode 140. However, as described above, the capillary passage can have other alternative constructions, such as a monolithic or multi-layer construction, which include a heater such as a resistance heating material positioned to heat the fluid in the capillary passage. For example, the resistance heating material can be disposed inside of, or exterior to, the capillary passage.

The capillary passage 160 may comprise an electrically conductive tube provided with the electrode 138, which is the downstream electrode, and the electrode 140, which is the upstream electrode. Both electrodes are preferably made of copper or a copper-based material. In this embodiment, the capillary 160 is a controlled temperature profile construction, such as disclosed in copending and commonly assigned U.S. application Ser. No. 09/957,026, filed Sep. 21, 2001, which is incorporated herein by reference in its entirety. In the controlled temperature profile capillary, the electrode 138 has an electrical resistance sufficient to cause it to be heated during operation of the aerosol generating device, thereby minimizing heat loss at the outlet end of the capillary tube.

The tube forming the capillary passage can be made entirely of stainless steel or any other suitable electrically conductive materials. Alternatively, the tube can be made of a non-conductive or semi-conductive material incorporating a heater made from an electrically conductive material, such as platinum. Electrodes connected at spaced positions along the length of the tube or heater define a heated region between the electrodes. A voltage applied between the two electrodes generates heat in the heated region of the capillary passage based on the resistivity of the material(s) making up the tube or heater, and other parameters such as the cross-sectional area and length of the heated region section. As the fluid flows through the capillary passage into the heated region between the first and second electrodes, the fluid is heated and converted to a vapor. The vapor passes from the heated region of the capillary passage and exits from the outlet end. If the volatilized fluid is entrained in ambient air as the volatilized fluid exits from the outlet, the volatilized fluid preferably condenses into small droplets, thereby forming a condensation aerosol. In a preferred embodiment, the MMAD of the droplet size is 0.5 to 2.5 µm.

The temperature of the liquid in the capillary passage can be calculated based on the measured or calculated resistance of the heating element. For example, the heating element can be a portion of a metal tube, or alternatively a strip or coil of resistance heating material. Control electronics can be used to regulate the temperature of the capillary passage by monitoring the resistance of the heater.

Resistance control can be based on the simple principle that the resistance of the heater increases as its temperature increases. As power is applied to the heating element, its temperature increases because of resistive heating and the actual resistance of the heater also increases. When the power is turned off, the temperature of the heater decreases and correspondingly its resistance decreases. Thus, by monitoring a parameter of the heater (e.g., voltage across the heater using known current to calculate resistance) and controlling application of power, the control electronics can maintain the heater at a temperature that corresponds to a specified resistance target. The use of one or more resistive elements could also be used to monitor temperature of the heated liquid in cases where a resistance heater is not used to heat the liquid in the capillary passage.

The resistance target is selected to correspond to a temperature that is sufficient to cause heat transfer to the liquid material such that liquid is volatilized and expands out the open end of the capillary passage. The control electronics activates the heating, such as by applying for a duration of time, pulsed energy to the heater and after and/or during such duration, determines the real time resistance of the heater, using input from the measuring device. The temperature of the heater can thus be calculated using a software program designed to correlate measured resistance of the heater. In this embodiment, the resistance of the heater is calculated by measuring the voltage across a shunt resistor (not shown) in series with the heater (to thereby determine current flowing to the heater) and measuring the voltage drop across the heater (to thereby determine resistance based on the measured voltage and current flowing through the shunt resistor). To obtain continuous measurement, a small amount of current can be continually passed through the shunt resistor and heater for purposes of making the resistance calculation and pulses of higher current can be used to effect heating of the heater to the desired temperature.

If desired, the heater resistance can be derived from a measurement of current passing through the heater, or by other techniques used to obtain the same information. The control electronics then makes decisions as to whether or not to send an additional duration of energy based on the difference between desired resistance target for the heater and the actual resistance as determined by control electronics.

In a developmental model, the duration of power supplied to the heater was set at 1 msec. If the monitored resistance of the heater minus an adjustment value is less than the resistance target, another duration of energy is supplied to the heater. The adjustment value takes into account factors, such as, for example, heat loss of the heater when not activated, the error of the measuring device and the cyclic period of the controller and switching device. In effect, because the resistance of the heater varies as a function of its temperature, resistance control can be used to achieve temperature control.

In embodiments, the capillary passage 160 can be constructed of two or more pieces of 32 gauge, 304 stainless steel tubing. In this embodiment, the downstream electrode can be a 3.5 mm length of 29 gauge tubing, while the upstream electrode may have any geometry that minimizes the resistance of the electrode, such as gold (Au) plated copper (Cu) pins.

The control electronics 120 can control the temperature of the capillary passage 160 by monitoring the resistance of the heater used to heat the capillary passage 160. To illustrate operation of the aerosol generating device, a target temperature for the capillary passage 160 can be about 220° C. for purposes of vaporizing propylene glycol (PG). In this embodiment, the measured electrical resistance of the heated capillary passage 160 is preferably 0.4 ohms for a target temperature of about 220° C. In order to achieve a resistance of 0.4 ohms, the control electronics pulses power to the electrode 138. In an embodiment, the control electronics 120 measures voltage and current in order to calculate the resistance across a length of the capillary passage 160. If the control electronics determines that the resultant resistance is below the target value, the control electronics turns power on for a selected period of time, e.g., 1 millisecond. The control electronics continues to repeat this process until the target resistance for the capillary passage 160 is reached. Likewise, if the control electronics determines that the resistance is higher than required for the temperature of the capillary passage 160, the control electronics turns off power for a selected period of time, e.g., 1 millisecond.

In this embodiment, the control electronics 120 may include any processor capable of controlling the resistance of the capillary passage 160 via the electrodes 138 and 140, such as a microchip PIC16F877, available from Microchip Technology Inc., located in Chandler, Ariz., which is programmed in assembly language.

As shown in FIGS. 4 and 5, the pressure sensor 122 is in fluid communication with the mouthpiece 134 via the air passage 132. The air passage 132 includes the air inlet 124 through which ambient air within the housing is drawn into the air passage 132 by a user inhaling on the mouthpiece 134. In a preferred embodiment, the aerosol generating device 100 is activated by a user inhaling on an outlet 144 of the mouthpiece 134. This inhalation causes a differential pressure in the air passage 132, which is sensed by the pressure sensor 122. The pressure sensor 122 can be extremely sensitive. For example, the pressure sensor can be triggered at a selected threshold value of air flow through the air passage 132, for example, as low as about 3 liters/min. This value equals less than about $\frac{1}{10}$ of the typical human inhalation flow rate. Accordingly, the user can trigger the pressure sensor without wasting appreciable lung volume.

Alternatively, the fluid delivery assembly 110 can be activated by a user manually depressing the switch 128.

The pressure sensor 122 or switch 128 activates the fluid delivery assembly 110 to cause liquid 153 (e.g., liquid medicament including a drug and liquid carrier) to flow from the liquid source 106 to the capillary passage 160 of the heater unit 130. The fluid is heated in the capillary passage 160 by the heater to a sufficiently high temperature to vaporize the liquid. Ambient air is delivered through the air passage 132 to a region 146 proximate to the outlet end of the capillary passage, at which the vapor is admixed with the ambient air to produce an aerosol.

In alternative embodiments, a pressurized air source can be used with the aerosol generating device to provide dilution air to mix with the aerosol. For example, the pressurized air source can be a compressed air source located within the aerosol generating device (not shown), a fan/blower to flow air into the mouthpiece, or any other suitable device.

The control electronics 120 can perform various selected functions in the aerosol generating device 100. For example, the control electronics 120 can control the temperature profile of the capillary passage 160 during operation of the aerosol generating device 100. The control electronics 120 can also control the output of the display 114. The display is preferably a liquid crystal display (LCD). The display can depict selected information pertaining to the condition or operation of the aerosol generating device 100. The control electronics can also control the operation of the inlet valve 156, discharge member 164 and outlet valve 158 during operation of the aerosol generating device 100; monitor the initial pressure drop caused by inhalation and sensed by the pressure sensor 122; and monitor the condition of the battery unit 116 that provides electrical power to components of the aerosol generating device.

In the embodiment shown in FIG. 4, the battery unit 116 can be, for example, a rechargeable battery, such as a 6 volt nickel metal hydride (NiMH) battery pack including multiple cells. In this embodiment, the battery unit includes multiple batteries (e.g., Sanyo HF-C1U, 600 mAh NiMH batteries) in series, which provides sufficient energy to operate the aerosol generating device for delivery of at least 100 doses of 5 µl volumes of medicament. The battery unit is preferably rechargeable via the charging jack 118. The battery unit provides power to components of the aerosol generating device (e.g., the control electronics 120, pressure sensor 122, etc.) and the master on/off switch.

The master on/off switch controls powering up and powering down of the aerosol generating device 100 during operation. The master on/off switch also activates the display 114. In an embodiment, the display provides information including, for example, the number of doses remaining within the liquid source 106, a failure of the heater unit 130, and a detected low voltage condition of the battery unit 116. The control electronics 120 can also include functionality via the processor for displaying the number of remaining doses, information on patient compliance, lockout times and/or child safety locks.

During operation of the aerosol generating device 100, a user removes the cap 104 to activate components of the aerosol generating device and expose the mouthpiece 134. The user activates switch 128, or inhales on the mouthpiece, which creates a pressure drop in the interior of the mouthpiece. This pressure drop is detected by the pressure sensor 122, which then sends a signal to a controller included in the control electronics 120, which operates the fluid delivery assembly 110.

The metering chamber 162 is filled and emptied by actuation of the discharge member 164. Closing of the discharge member 164 with the inlet valve 156 closed and the outlet valve 158 opened empties liquid in the metering chamber 162, which forces liquid present in the flow passage 150 downstream of the metering chamber into the capillary passage 160. The metering chamber 162 ensures that a desired volume of liquid in aerosol form is delivered by the aerosol generating device 100 to the user. The metering chamber can have a selected dose volume of, e.g., 5 µl. However, the metering chamber can have any desired volume depending upon the application of the aerosol generating device 100. After delivery of the desired volume of the medicament to the capillary passage 160, the outlet valve 158 is closed, and the flow passage 150 is refilled with liquid from the liquid source 106.

During a fill cycle of the aerosol generating device 100, the metering chamber 162 is filled with liquid from the liquid source 106. During the fill cycle, the inlet valve 156 is opened and the outlet valve 158 is closed, while the discharge member 164 is opened to allow the liquid to fill the metering chamber 162.

During delivery of the liquid to the capillary passage 160, the inlet valve 156 is closed. As the inlet valve 156 closes, the outlet valve 158 is opened, while the discharge member 164 is closed to empty the metering chamber 162 and force liquid from the flow passage 150 into the heated capillary passage 160.

Liquid flows through the heated capillary passage 160 and exits from the outlet section as a vapor. At the exit of the capillary passage 160, ambient air provided via the air passage 132 admixes with vapor to form an aerosol such as a condensation aerosol.

As described further below, the particle size of the aerosol can be controlled by selection of the size of the outlet section of the capillary passage. The aerosol generating device can also produce aerosols with high number concentrations. Preferably, the aerosol particles have a MMAD between about 0.5 µm and about 2.5 µm. As described above, the aerosol generating device can provide aerosols having a controlled particle size, including aerosols sized for the targeted delivery of drugs to the lung. These aerosols offer a number of advantages for delivering drugs to the deep lung. For example, mouth and throat deposition are minimized, while deposition in the deep lung is maximized, especially when combined with a breath hold. Moreover, when using a suitable hydrophilic carrier, deposition may be further enhanced by hygroscopic growth.

The aerosol generating device preferably generates aerosols in which 95% of the aerosol particles (aerosol droplets) are in the range between about 0.5 µm to about 2.5 µm. The aerosol generating device preferably incorporates a processor chip for controlling the generation process. The processor, with suitable sensors, also triggers the aerosol generation at any desired time during an inhalation. The drug to be aerosolized is provided with a carrier. By the choice of suitable hydrophilic carriers, the aerosol generating device can take advantage of hygroscopic growth in the respiratory system.

Operation of the preferred aerosol generating device for delivering aerosolized medicaments is as follows. First, a liquid carrier is delivered to the heated capillary passage along with a drug. The liquid vaporizes in the capillary passage and exits as a vapor jet from the open end of the capillary passage. The vapor jet entrains and mixes with ambient air and forms an aerosol, e.g., the vapor cools and then condenses to form a highly concentrated, fine aerosol. As described above, application of heat to vaporize the liquid is typically achieved by resistive heating from passing an electric current through the heater. The applied power is adjusted to maximize the conversion of the fluid into a vapor.

The aerosol generating device can form aerosols over a range of fluid flow rates dependent on the size of the capillary passage and the power available to vaporize the liquid. A liquid that may be used to demonstrate aerosol generation for drug delivery is propylene glycol (PG) obtained as USP grade (CAS # 57-55-6) from Fisher Scientific in Atlanta, Ga. PG has a boiling point of 189° C. and a density of 1.036 g/mL. Solute compounds used as models for drugs include triphenylmethane (CAS # 519-73-3) and oleyl alcohol (OA) (CAS #143-28-2) also available from Fisher Scientific in Atlanta, Ga.

Adding a solute, such as a drug, to PG can change the condensation process because the solute may act as nucleating agent for the PG. If the solute has a vapor pressure similar to the PG, the solute condenses in the aerosol at the same time that the PG condenses.

In an exemplary embodiment in which the solute is less volatile than PG, the solute may start the condensation process early and serve as a nucleating agent for subsequent PG condensation. In this embodiment, a difference between the chemical distribution of the solute and the mass distribution of the overall aerosol may occur. This manifests itself in different MMADs for the solute and the PG. These are not two separate aerosols; rather, one aerosol is produced having a varying chemical composition as a function of size. The MMADs can be a function of the solute concentration.

As will be appreciated, the aerosol generating device is capable of controlled vaporization and aerosolization of drug formulations. The aerosol generating device can provide immediate delivery of aerosol to a patient, thereby not wasting lung capacity, which may be limited due to the health of the patient. Also, the aerosol generating device can provide consistent delivery of controlled amounts of drug formulation to a patient.

EXAMPLE 1

Tests were conducted to demonstrate that the exit velocity of vapor from the capillary passage of the aerosol generating device is related to the particle size of the aerosol that is formed from the vapor. Capillaries A, B and C, each having a tubular construction and having respective capillary passage nominal diameters of 0.15 mm, 0.22 mm and 0.27 mm, were used to form aerosols. Capillaries A, B and C did not include an outlet section to change the velocity of the vapor.

Figure 11:
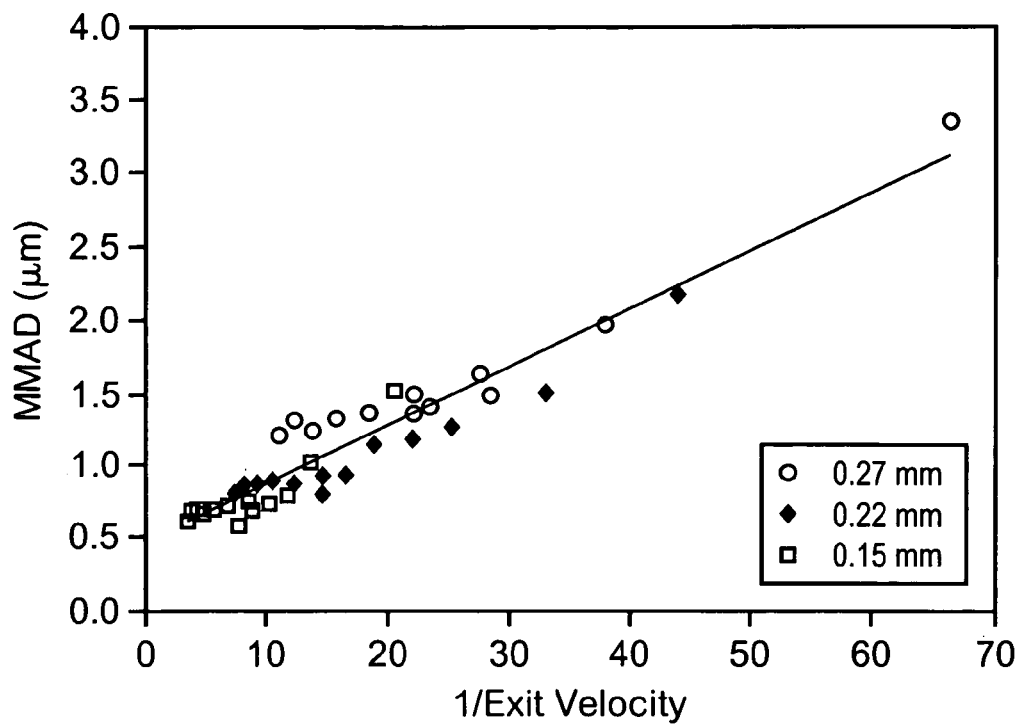
FIG. 11 illustrates the relationship between the mass mean aerodynamic diameter (MMAD) of aerosol particles and the inverse of the exit velocity of vapor used to form aerosols generated from propylene glycol.

Aerosols were generated from 100% propylene glycol using capillaries A, B and C. FIG. 11 shows the relationship between the MMAD of the aerosol particles and the inverse of the exit velocity of the vapor from the capillary passage for capillaries A, B and C. As shown, for each of the three capillary passage diameters, the MMAD of the aerosol particles increased linearly with the inverse of the exit velocity, i.e., a decrease in the exit velocity. These experimental results demonstrate that by controlling the exit velocity of the vapor, the particle size of the aerosols can be controlled.

EXAMPLE 2

Tests were also performed to demonstrate the effect of adding an outlet section to the capillary passage on the aerosol particle size. Capillaries D, E and F having a tubular construction were used. Capillary D did not include an outlet section and had a capillary passage nominal diameter of 0.22 mm. Capillary E included a first section (piece) of capillary of the same capillary passage diameter as capillary D, and an outlet section in the form of a capillary tube having a larger capillary passage nominal diameter of 0.4 mm secured to the first section to form a capillary passage having a configuration similar to that of the capillary passage 260 shown in FIG. 6. Capillary F included a first section having a nominal capillary passage diameter of 0.15 mm and an outlet section having a larger nominal capillary passage diameter of 0.27 mm secured to the first section. Table 1 shows the diameter of the capillary passage of the first section and the outlet section, and the total length of the capillary passage for capillaries D, E and F.

TABLE 1

| Capillary | First Section Capillary Passage Diameter (mm) | Outlet section Capillary Passage Diameter (mm) | Capillary Length (mm) |
|---|---|---|---|
| D | 0.22 | — | 24 |
| E | 0.22 | 0.4 | 24 |
| F | 0.15 | 0.27 | 24 |

A heater was positioned relative to the capillary passage of capillaries D, E and F to heat fluid introduced into the capillary passage to a sufficiently high temperature to vaporize the liquid. The liquid used was propylene glycol containing various contents of oleyl alcohol. The liquid was vaporized in capillaries D–F to determine the relationship between the MMAD of the aerosol particles of the generated aerosols and the exit velocity of the fluid (vapor) exiting the capillary passages.

Figure 12:
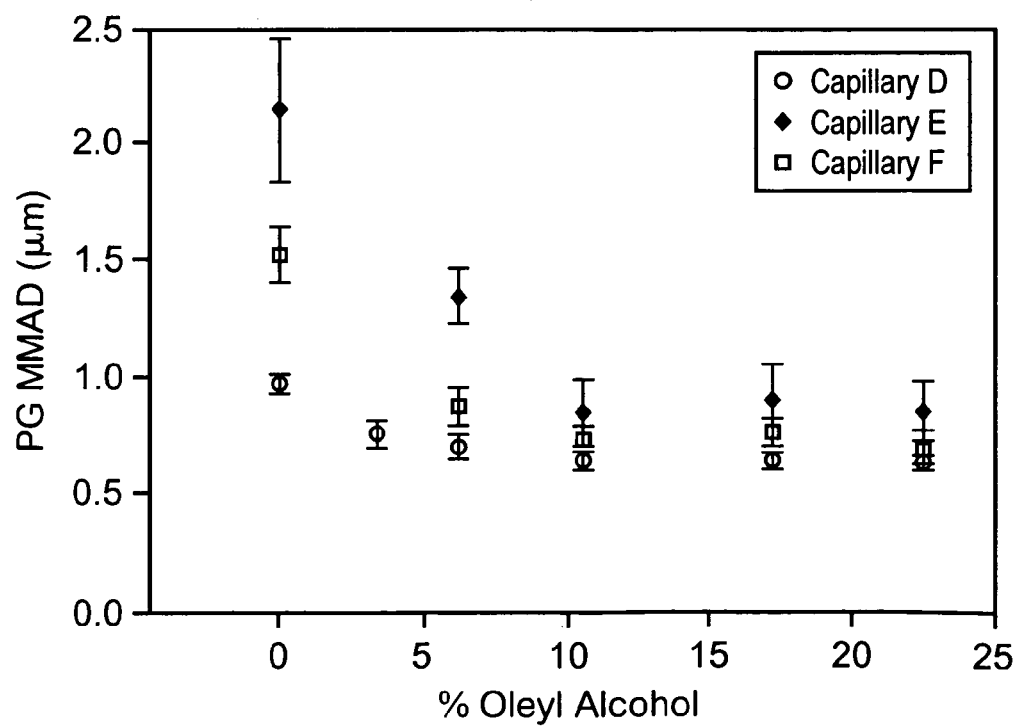
FIG. 12 illustrates the relationship between the MMAD of aerosolized propylene glycol (PG) and the percentage of oleyl alcohol (OA) in the propylene glycol.
Figure 13:
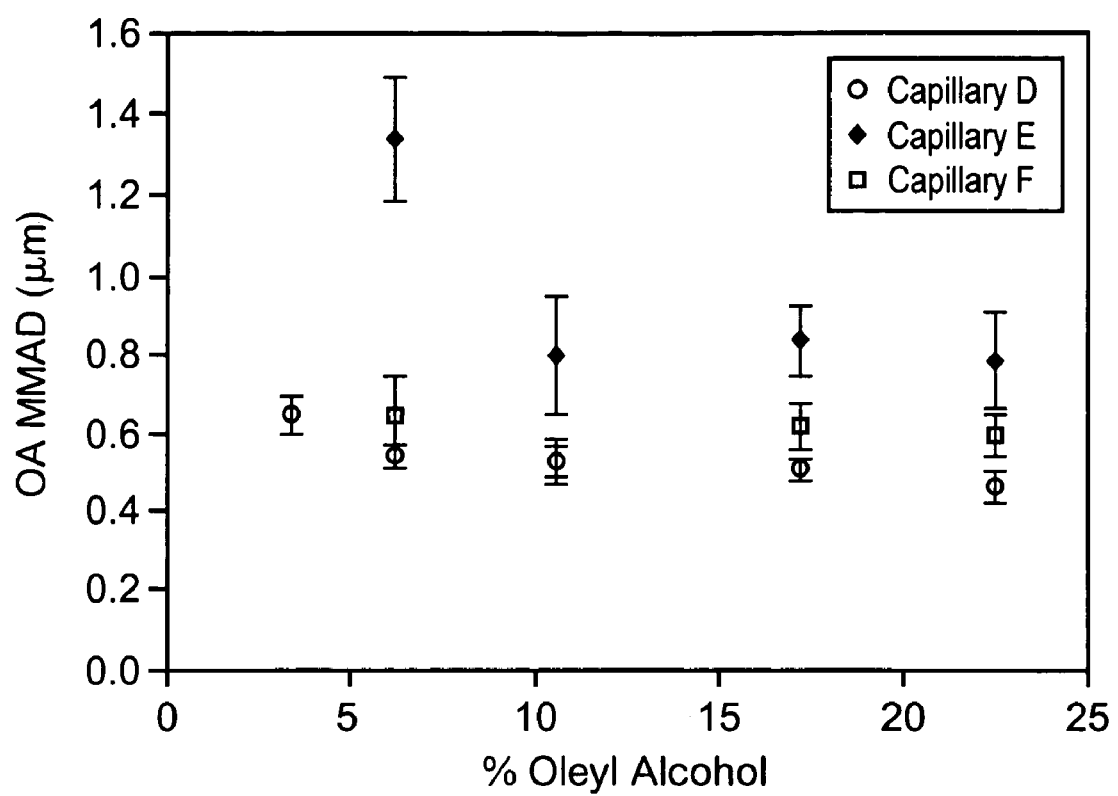
FIG. 13 illustrates the relationship between the MMAD of aerosolized oleyl alcohol and the percentage of oleyl alcohol in propylene glycol.

FIGS. 12 and 13 show the test results. FIG. 12 illustrates the relationship between the MMAD of aerosolized propylene glycol (PG) having various percentages of oleyl alcohol in the propylene glycol. As shown in FIG. 12, capillary E including the largest diameter capillary passage outlet section produced the largest MMAD for the aerosolized liquid, while capillary D without an outlet section produced the smallest MMAD. Also, for each of the capillaries D, E and F, the MMAD decreased significantly as the oleyl alcohol content varied from 0% to 10%, but did not significantly change at higher oleyl alcohol contents.

FIG. 13 illustrates the relationship between the MMAD of aerosolized oleyl alcohol (OA) in PG and various percentages of oleyl alcohol in the PG. As shown in FIG. 13, capillary E also produced the largest MMAD for the aerosolized liquid, while capillary D produced the smallest MMAD.

Accordingly, the results clearly demonstrate that by incorporating an outlet section in the capillary passage, the particle size of the aerosol can be controlled. Further, by varying the size of the flow passage defined by the outlet section, the aerosol particle size can be further controlled.

EXAMPLE 3

A one-piece capillary G having a constant diameter and a one-piece capillary H having a configuration similar to the capillary passage 560 shown in FIG. 9 were tested to further demonstrate the effect of the outlet section on the particle size of PG aerosol particles produced using the capillaries. Particularly, capillary G had a constant capillary passage diameter of 0.22 mm along its length. Capillary H included a first section having a capillary passage nominal diameter of 0.22 mm and an outlet section at the outlet end having a capillary passage diameter larger than 0.22 mm. For capillary G, the measured MMAD values for the aerosol particles ranged from about 1.1 to about 1.3 microns. For capillary H, the measured MMAD values for the aerosol particles ranged from about 2.2 to 2.6 microns. These test results further demonstrate that by incorporating an outlet section in the capillary passage, the particle size of the aerosol can be controlled.

The above-described exemplary modes of carrying out the invention are not intended to be limiting. It will be apparent to those of ordinary skill in the art that modifications thereto can be made without departure from the spirit and scope of the invention as set forth in the accompanying claims. For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like.

What is claimed is:

1. An aerosol generating device, comprising:
 a liquid source;
 a flow passage in fluid communication with the liquid source, the flow passage including a heated portion and an outlet section disposed downstream of the heated portion and having an outlet end;
 a heater disposed to heat liquid in the heated portion of the flow passage to produce a vapor;
 a cower supply; and
 a controller operable to deliver power from the power supply to the heater to maintain the heater at a temperature range effective to vaporize the liquid in the heated portion of the flow passage to produce the vapor which flows from the heated portion into the outlet section;
 wherein the outlet section is configured to change the velocity of the vapor in the flow passage such that vapor exits the outlet end of the outlet section at a controlled exit velocity and forms an aerosol.

2. The aerosol generating device of claim 1, wherein the outlet section of the flow passage is configured to (i) increase the exit velocity of the vapor such that a mass mean aerodynamic diameter of aerosol particles is decreased, or (ii) decrease the exit velocity of the vapor such that the mass mean aerodynamic diameter of aerosol particles is increased.

3. The aerosol generating device of claim 1, wherein the outlet section is a material selected from group consisting of metals, plastics, polymers, ceramics, glasses, and combinations thereof.

4. The aerosol generating device of claim 1, wherein the outlet section is a different material than a portion of the flow passage adjacent to the outlet section.

5. The aerosol generating device of claim 1, wherein the outlet section is joined to a portion of the flow passage adjacent to the outlet section.

6. The aerosol generating device of claim 1, wherein the outlet section has a round or a non-round cross-sectional shape.

7. The aerosol generating device of claim 1, wherein the flow passage comprises a first section upstream from the outlet section, the first section has a smaller cross-sectional flow area than a cross-sectional flow area of the outlet section.

8. The aerosol generating device of claim 1, wherein the flow passage comprises a second outlet section upstream from the outlet section.

9. The aerosol generating device of claim 1, wherein the outlet section has a cross-sectional flow area which varies along a length of the outlet section.

10. The aerosol generating device of claim 9, wherein the cross-sectional flow area of the outlet section varies continuously or non-continuously along the length of the outlet section.

11. The aerosol generating device of claim 1, wherein the flow passage is a capillary sized flow passage.

12. The aerosol generating device of claim 1, further comprising at least one valve disposed between the liquid source and the flow passage, the controller being operable to actuate the valve to open and close the flow passage to control flow of the liquid from the liquid source to the flow passage.

13. The aerosol generating device of claim 1, further comprising:
 a mouthpiece through which the aerosol is inhaled by a user of the aerosol generating device;
 a pressure sensor;
 an air passage through which air is supplied into the mouthpiece; and
 a valve which opens and closes the air passage;
 wherein the controller is operable to actuate the valve within a predetermined time period after the pressure sensor detects a pressure drop in the mouthpiece as the user inhales on the mouthpiece to allow air to be supplied into the mouthpiece.

14. The aerosol generating device of claim 1, wherein the flow passage comprises a metering chamber having a predetermined volume, and the aerosol generating device comprises a discharge member operable to deliver an amount of the liquid equal to the predetermined volume into the heated portion of the flow passage.

15. The aerosol generating device of claim 1, wherein the liquid comprises a drug and a carrier.

16. The aerosol generating device of claim 1, which is a hand held inhaler.

17. The aerosol generating device of claim 1, wherein the liquid source, flow passage and heater comprise a fluid delivery assembly which is removably attached to the aerosol generating device.

18. A method of generating an aerosol, comprising:
    (a) supplying a liquid from a liquid source to a flow passage including a heated portion and an outlet section disposed downstream of the heated portion and having an outlet end;
    (b) controlling delivery of power from a power supply to a heater to maintain the heater at a selected temperature range to vaporize the liquid in the heated portion of the flow passage to produce a vapor which flows from the heated portion into the outlet section;
    (c) changing the velocity of the vapor in the outlet section such that the vapor exits the outlet end of the outlet section at a controlled exit velocity; and
    (d) admixing the vapor with air to produce an aerosol.

19. The method of claim 18, wherein (c) comprises controlling the exit velocity of the vapor from the outlet end of the outlet section to produce aerosol particles having a controlled particle size.

20. The method of claim 18, comprising changing the velocity of the vapor in the outlet section to (i) increase the exit velocity of the vapor such that a mass mean aerodynamic diameter of aerosol particles of the aerosol is decreased, or (ii) decrease the exit velocity of the vapor such that the mass mean aerodynamic diameter of aerosol particles is increased.

21. The method of claim 18, wherein aerosol particles of the aerosol have a mass mean aerodynamic diameter of less than 2.5 microns.

22. The method of claim 18, wherein the flow passage is a capillary sized flow passage.

23. The method of claim 18, further comprising:
    supplying a predetermined volume of the liquid into the heated portion of the flow passage; and
    heating the predetermined volume of the liquid to produce the vapor.

24. The method of claim 23, further comprising:
    detecting a pressure drop in a mouthpiece of the aerosol generating device caused by a user inhaling on the mouthpiece;
    supplying the predetermined volume of the liquid into the heated portion of the flow passage after detecting the pressure drop; and
    delivering the aerosol to the user through the mouthpiece.

25. The method of claim 18, comprising producing the aerosol continuously.

26. The method of claim 18, wherein the liquid comprises a drug and a carrier.

27. The method of claim 18, further comprising:
    performing (a)–(d) using a first fluid delivery assembly;
    removing the first fluid delivery assembly from the aerosol generating device;
    attaching a second fluid delivery assembly to the aerosol generating device; and
    repeating (a)–(d) using the second fluid delivery assembly.

28. The method of claim 27, wherein the first fluid delivery assembly supplies a first liquid, and the second fluid delivery assembly supplies a second liquid different from the first liquid.

29. The method of claim 27, comprising producing a first aerosol containing particles having a first mass mean aerodynamic diameter with the first fluid delivery assembly, and producing a second aerosol containing particles having a second mass mean aerodynamic diameter different from the first mass mean aerodynamic diameter with the second fluid delivery assembly.

30. The method of claim 27, wherein the first fluid delivery assembly comprises a first outlet section having a first outlet end with a first cross-sectional flow area, and the second fluid delivery assembly comprises a second outlet section having a second outlet end with a second cross-sectional flow area different from the first cross-sectional area.

31. The aerosol generating device of claim 1, wherein the flow passage has a maximum width of from 0.05 mm to 1 mm.

32. The aerosol generating device of claim 1, wherein the flow passage has a length of from 0.5 cm to 10 cm.

33. The aerosol generating device of claim 1, wherein the flow passage is capillary sized and comprises a capillary tube, a monolithic body, or a multilayer structure.

34. The aerosol generating device of claim 1, wherein the flow passage has a one-piece construction.

35. The aerosol generating device of claim 1, wherein the heated portion is attached to the outlet section.

36. An aerosol generating device, comprising:
    a capillary sized flow passage adapted to be in fluid communication with a liquid source, the flow passage including a first section upstream from an outlet section having an outlet end;
    a heater disposed to heat liquid in the first section of the flow passage to produce a vapor;
    a power supply; and
    a controller operable to deliver power from the power supply to the heater to maintain the heater at a temperature range effective to vaporize the liquid in the first section of the flow passage to produce a vapor which flows from the first section into the outlet section;
    wherein the outlet section has a cross-sectional flow area that is smaller than a cross-sectional flow area of the first section, the outlet section changing the velocity of the vapor in the flow passage such that vapor exits the outlet end at a controlled exit velocity and forms an aerosol.

37. The aerosol generating device of claim 36, further comprising a liquid source in fluid communication with the flow passage, wherein the flow passage has a maximum width of from 0.05 mm to 1 mm.

38. The aerosol generating device of claim 36, wherein the flow passage has a length of from 0.5 cm to 10 cm.

39. The aerosol generating device of claim 36, wherein the flow passage comprises a capillary tube or a multilayer structure.

40. The aerosol generating device of claim 36, wherein the flow passage has a one-piece construction.

41. The aerosol generating device of claim 36, wherein the outlet section is removably or fixedly attached to the first section.

42. The aerosol generating device of claim 36, wherein the cross-sectional flow area of the outlet section varies continuously or non-continuously along a length of the outlet section.

43. The aerosol generating device of claim 7, wherein the first section of the flow passage has a greater cross-sectional flow area than a cross-sectional flow area of the outlet section of the flow passage.

* * * * *